(12) United States Patent
Polat

(10) Patent No.: US 8,403,485 B2
(45) Date of Patent: Mar. 26, 2013

(54) SYSTEM AND METHOD FOR VISION EVALUATION

(75) Inventor: Uri Polat, Ramat Gan (IL)

(73) Assignee: Ucansi Inc., New York, NY (US)

( * ) Notice: Subject to any disclaimer, the term of this patent is extended or adjusted under 35 U.S.C. 154(b) by 309 days.

(21) Appl. No.: 12/954,948

(22) Filed: Nov. 29, 2010

(65) Prior Publication Data

US 2011/0116047 A1    May 19, 2011

Related U.S. Application Data

(63) Continuation-in-part of application No. 11/885,229, filed as application No. PCT/IL2005/000927 on Aug. 31, 2005, now Pat. No. 7,866,817.

(60) Provisional application No. 60/607,081, filed on Sep. 3, 2004.

(51) Int. Cl.
*A61B 3/02* (2006.01)
(52) U.S. Cl. .......... 351/239; 351/242; 351/246
(58) Field of Classification Search .......... 351/203, 351/222, 237, 238, 239, 242, 246
See application file for complete search history.

(56) References Cited

U.S. PATENT DOCUMENTS

| | | | |
|---|---|---|---|
| 5,051,931 A | 9/1991 | Cheu et al. | |
| 5,088,810 A | 2/1992 | Galanter et al. | |
| 5,121,981 A | 6/1992 | Waltuck et al. | |
| 5,308,246 A | 5/1994 | Belocco | |
| 6,464,356 B1 | 10/2002 | Sabel et al. | |
| 6,876,758 B1 | 4/2005 | Polat | |
| 7,004,912 B2 | 2/2006 | Polat | |
| 7,187,363 B2 | 3/2007 | Nguyen et al. | |
| 7,346,856 B2 | 3/2008 | Nguyen et al. | |
| 7,661,821 B2 | 2/2010 | Ellenbogen | |
| 8,083,354 B2 * | 12/2011 | Derr .............................. | 351/246 |
| 2003/0109800 A1 | 6/2003 | Polat | |
| 2003/0232319 A1 | 12/2003 | Grisham et al. | |
| 2004/0165145 A1 | 8/2004 | Hatanaka et al. | |
| 2007/0200927 A1 | 8/2007 | Krenik | |
| 2008/0189173 A1 | 8/2008 | Bakar et al. | |

FOREIGN PATENT DOCUMENTS

| | | |
|---|---|---|
| JP | 11-47208 | 2/1999 |
| JP | 2000-157586 | 3/2000 |
| JP | 2001-54587 | 2/2001 |
| WO | WO 01/47463 | 7/2001 |
| WO | WO 03/092482 | 8/2003 |

OTHER PUBLICATIONS

Zenger et al. 'Isolating Excitatory and Inhibitory Nonlinear Spatial Interactions Involved in Contrast Detection', Vision Res. vol. 36, No. 16, pp. 2497-2513, 1996.

Adini et al. 'Excitatory-inhibitory network in the visual cortex: psychophysical evidence', Proc. Natl. Acad. Sci. USA, Neurobiology, vol. 94, pp. 10426-10431, Sep. 1997.

(Continued)

*Primary Examiner* — Huy K Mai
(74) *Attorney, Agent, or Firm* — Pearl Cohen Zedek Latzer, LLP; Mark S. Cohen

(57) ABSTRACT

A method for vision evaluation including displaying a sequence of frames on a display screen of a display device. Each frame may contain one or more symbols. The method may also include changing one or more viewing parameters between frames of said sequence of frames as the displaying of the sequence of frames progresses. The viewing parameters may be selected from the group of viewing parameters consisting of spatial and temporal parameters. The method may also include calculating a vision evaluation score for the subject whose response to the displayed sequence of frames is received through an input interface device. A system for vision evaluation is also disclosed.

13 Claims, 13 Drawing Sheets

OTHER PUBLICATIONS

Polat U., Sagi D. (1993) Lateral interactions between spatial channels: suppression and facilitation revealed by lateral masking experiments. *Vision Res.*, 33(7), 993-999.

Polat U., Sagi D. (1994) The architecture of perceptual interactions. *Vision Res.*, 34(1), 73-78.

Polat U., Sagi D. (1994) Spatial interactions in human vision: from near to far via experience-dependent cascades of connections. *Proc. Natl. Acad. Sci. USA*, 91, 1206-1209.

Polat U., Norcia A.M. (1996) Neurophysiological evidence for contrast dependent long range facilitation and suppression in the human visual cortex. *Vision Res.*, 36, pp. 2099-2109.

Levi D.M., Polat U. (1996) Neural plasticity in adults with amblyopia. *Proc. Natl. Acad. Sci. USA*, 93, pp. 6830-6834.

Polat U., Sagi D., Norcia A.M. (1997) Abnormal long-range spatial interations in amblyopia. *Vision Res.*, 37, pp. 737-744.

Levi D.M., Polat U., Hu YS, (1997) Visual improvements with amblyopia. *Invest. Ophthalmol. Vis. Sci.*, 38(8) 1493-1510.

Polat U., (1999) Functional architecture of long-range perceptual interactions. *Spatial Vision*, 12, 143-162.

Polat, U., Ma-Naim, T., Belkin, M., & Sagi, D. (2004) Improving vision in adult amblyopia by perceptual learning. *Proc Natl Acad Sci U S A*, 101(17): 6692-6697.

Bonneh, Y., Sagi, D., Polat, U. (2004) Local and non-local deficits in amblyopia: acuity and spatial interactions. *Vision Res* 44(27), 3099-310.

Tanaka Y. and Sagi D. (1998) Long-lasting, long-range detection facilitation. Vision Research 38. 2591-2599.

International Search Report for WO 2006/025056 dated Mar. 23, 2006.

International Search Report for PCT Application No. PCT/IL2011/000803 mailed May 1, 2012.

\* cited by examiner 610    620    630

SYSTEM AND METHOD FOR VISION EVALUATION

CROSS REFERENCE TO RELATED APPLICATIONS

This application is a continuation-in-part of U.S. patent application Ser. No. 11/885,229, filed on Dec. 18, 2008, now U.S. Pat. No. 7,866,817 which was a National Phase Application of PCT International Application No. PCT/IL2005/000927, International Filing Date Aug. 31, 2005, claiming priority of U.S. Provisional Patent Application 60/607,081, filed Sep. 3, 2004.

FIELD OF THE INVENTION

The present invention relates to vision evaluation. More particularly, the present invention relates to system and method for vision evaluation.

BACKGROUND OF THE INVENTION

Human eyesight is a product of two separate processes that work together to form images for a person to "see." One of these processes, herein referred to as the physical component, concerns the physical structure of the various elements of the eye and how incoming light is manipulated and processed by the eye. Defects in the shape of the cornea, the retinal wall, or the optic nerve can impair the functionality of a person's eye and thus impair or eliminate the ability to perceive images. Some of these defects can be corrected through the use of glasses, contact lenses, or surgery.

The second process involved in allowing humans to see images is herein referred to as the neurological component. This component concerns neural processing in the brain and how the brain analyzes information sent from the eyes to produce an image. A person can likewise have a number of defects in this component of the visual process.

The physical component and the neurological component work together to form images that a person sees, or more precisely, that a person perceives. The term "perceives" is preferred because, although the physical component may capture certain details, defects in the neurological component may distort and destroy these details. Alternatively, efficient performance of the neurological component may enhance the image; therefore, the image that is "seen" by the person may not be exactly what the eyes capture. Consequently, the image that is perceived may differ in detail from the image that is seen by the eyes. Thus, the overall process of human eyesight is herein referred to as the visual perception process.

It has been shown that training may improve visual perception of a human subject. These training generally involve displaying images to the trainee.

United States Patent Application 20030109800 to Polat, Uri titled "Systems and methods for improving visual perception" describes a method for improving a common defect in the neurological component of the visual perception process known as amblyopia. This application was published as U.S. Pat. No. 6,876,758 "Methods and systems for improving a user's visual perception over a communications network" to Polat et al., Apr. 5, 2005; and is incorporated herein by reference.

U.S. Pat. No. 6,464,356 by B. A. Sabel et al., entitled Process and device for the training of human vision; Oct. 15, 2002; Filed: Apr. 25, 2001, present a process for training the visual system of a human having a zone of intact vision and a zone of deteriorated vision.

Image display apparatus used in the art for training are generally bulky and cannot easily be carried by the trainee.

SUMMARY OF THE INVENTION

According to embodiments of the present invention a method for vision evaluation may include displaying a sequence of frames on a display screen of a display device. Each frame may contain one or more symbols. The method may further include changing one or more viewing parameters between frames of said sequence of frames as the displaying of the sequence of frames progresses. The viewing parameters may be selected from the group of viewing parameters consisting of spatial and temporal parameters. The method may also include calculating a vision evaluation score for the subject whose response to the displayed sequence of frames is received through an input interface device.

In accordance with embodiments of the present invention, the viewing parameters may be selected from a group of viewing parameters consisting of: physical size of the symbols, duration of presentation of each frame, contrast of each frame, color of the symbols, color of a background of one or more frames, number of symbols in each frame and display resolution of each frame.

In accordance with embodiments of the present invention, the calculated score may include diopter value for one or more spectacle lenses for the subject.

In accordance with embodiments of the present invention, the changing of the viewing parameters of the sequence of frames as the displaying of the sequence of frames progresses may be carried out between consecutive frames.

In accordance with embodiments of the present invention, the calculation of the vision evaluation score may carried out on a remote device communicating via a network with the display device.

In accordance with embodiments of the present invention, the displaying of the sequence of frames comprising using a staircase technique.

In accordance with embodiments of the present invention, a system for vision evaluation may include a display device for displaying a sequence of frames on a display screen of the display device. Each frame may contain one or more symbols. The display may be also used for changing one or more viewing parameters between frames as the displaying of the sequence of frames progresses. The viewing parameters may be selected from the group of viewing parameters consisting of spatial and temporal parameters. The system may also include a processing unit for calculating a vision evaluation score for the subject whose response to the displayed sequence of frames is received through an input interface device.

BRIEF DESCRIPTION OF THE DRAWINGS

An exemplary embodiment of the invention is described in the following section with respect to the drawings. The same reference numbers are used to designate the same or related features on different drawings. The drawings are generally not drawn to scale.

DETAILED DESCRIPTION OF EXEMPLARY EMBODIMENTS

The following detailed description is of the best presently contemplated modes of carrying out the present invention. This description is not to be taken in a limiting sense, but is made merely for the purpose of illustrating the general principles in accordance with the present invention. The scope of the present invention is best defined by the appended claims.

Hand Held Device.

Figure 1:
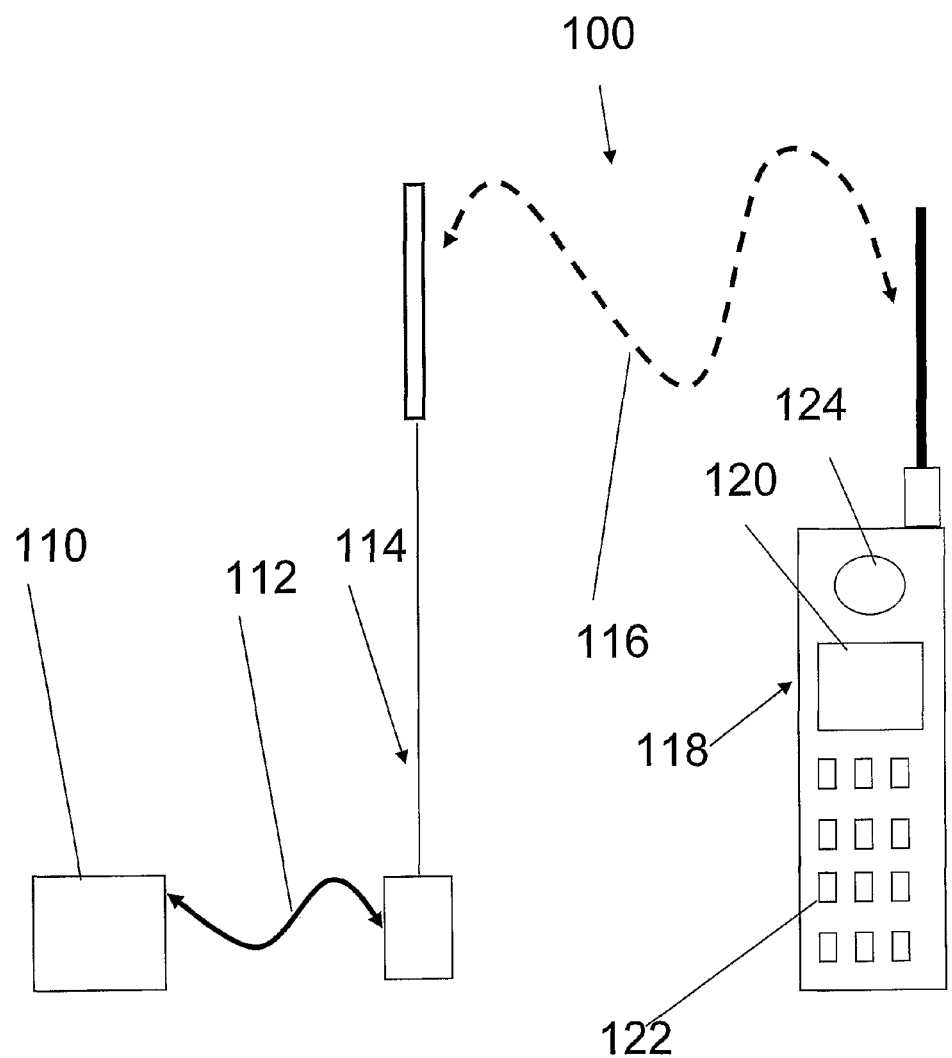
FIG. 1 shows a system for training the visual system of a human by presenting on a hand held display unit visual stimuli to the human according to an exemplary embodiment of the invention.

With reference to the drawings, in FIG. 1 is an illustration of a system 100 for training the visual system of a human by presenting on a hand held display unit visual stimuli to the human according to an exemplary embodiment of the invention.

In this exemplary embodiment, the trainee uses a hand held device 118 such as a cellular phone to view visual stimuli. The visual stimuli are generated by a program installed in the hand held device according to parameters stored in the hand held device. Said program controls the hand held device during the training session.

Alternatively, the hand held device 118 may be a palm computer, pocket PC, PDA, electronic notebook, iPod player or alike.

The hand held display unit device 118 comprises a display 120 and user input means such as keypad 112. In a training session, the trainee is asked to perform a visual task comprising observing the visual stimulus or a sequence of visual stimuli and respond to it.

The user input may optionally be received by the hand held device using other input means, for example: voice command using the built in microphone in a cellular phone, switches on a mobile "hands free" of headset attachments, touch screen sensor in a pocket PC, palm computer or PDA or other input means which are part of or connected to the hand held device 118.

The hand held device analyzes the user response to determine if the response was correct according to criteria associated with this task.

Criteria associated with this task may comprise reaction time of the user to the stimuli. Long delayed reaction may indicate slow visual processing by the user, while abnormally fast reaction may indicate that the user is guessing without actually perceiving the image.

Optionally, as a response to the user input, the program generates a feedback to be transmitted to the user using plurality of output means.

The output means may be one or few of: audio or visual output means with which the hand held device is equipped. For example, a text or pictorial message may be displayed on the screen 120, a sound or voice message can be generated using a speaker 124. Additionally or alternatively, other output means may be used such as vibration, ring tone or signaling lights whenever available.

Optionally, the feedback provided by the program may comprise encouraging statements such as "good progress" to encourage the trainee to use the application efficiently.

Some accessories may optionally be used with the hand held device. For example, a headset or a hands free attachment could be connected to cellular phone used as the hand held device in accordance to the embodiment of the invention. A head set usually comprises an earphone, a microphone and at least one pushbutton key which may be used as input-output means for receiving user input, for example by the microphone and/or pushbutton, and providing feedback as sound or voice through the earphone. Corded head set or wireless head set, such as "blue tooth" headset may be used. Optionally other accessories such as large screen display may be used.

The distance between the display 120 and the trainee's eye may vary depending on the visual deficiency and the type of training. In some training session the trainee is instructed to hold the hand held device at arm length away. In this situation, the display may occupy approximately ten degrees of the visual field. In contrast to larger displays such as computer screens used in the art, small display used for example in of a cellular phone, when held at distance of approximately 0.5 meter or more, provides training to the central field of view only.

In order to improve near-sight capability, the trainee may be requested to hold the hand held device at shorter distance from his eye, such as 30 or 40 cm. Alternatively, the trainee may be told to position the hand held device at larger distance such as one meter and more. In this case, input/output accessory is preferably used.

The trainee may be requested to remove his glasses or contact lenses for the duration of the session or requested to wear special glasses. Each eye may be trained separately by covering the other eye, or both eyes may be trained as once.

Network Connection to the Server

In one embodiment of the invention the system 100 comprises of a server computer 110.

The server 110 may, from time to time, be connected to the hand held device for example by using Internet and/or phone network to connect to a cellular base station 114 and radio wave to connect to the hand held device.

Alternatively, hand held device 118 may connect locally to another computing device (not shown) which is connected to the server 110. For example, a palm computer may be connected to local PC via cable, IR or RF and the local PC connects to the server using for example a telephone modem, ADSL, LAN or other means. In this way, messages between the server and the hand held device may be exchanged. Messages may be exchanged in this manner even if both connections are not simultaneously active. Various communication protocols may be used to exchange information between the server 110 and hand held device 118. For example, SMS and MMS are widely supported by the cellular networks and allow exchanging short text, data and images. Other, more wideband data exchange protocols exist.

The server, as will be detailed later, may perform various services for the hand held device. For example, the server may hold authorization codes to enable a session by the user holding the hand held device, the server may load the application program to the hand held device, or the server may monitor the training progress of the trainee by receiving and analyzing the user inputs from the hand held device, optionally modifying the program or parameters used to generate visual stimuli.

Optionally, the server is also used to provide billing information according to the utilization of the training application.

Method of Operation

With reference to the drawings, in FIGS. 2a and 2b are block diagrams of depicting the method according to the current invention. In these drawings, boxes marked by dashed lines represent optional steps and boxes marked by double lines represent steps in which information is tested and a decision is taken. Some optional steps are described in the text but not shown in the drawings.

2a is an illustration of a method for training the visual system of a human by presenting on a hand held display unit visual stimuli to the human according to an exemplary embodiment of the invention.

In order to be trained, the trainee must be registered with a provider of the training application.

Optionally, the registration 210 involves visiting the provider office or a clinic where optionally his visual capabilities are tested 212, preferably by a qualified personnel. Testing 210 may be done before or after the registration process, optionally at a different location. Alternatively, a trainee may be referred by his or her doctor or optometrist with a known diagnostics so that further testing is unnecessary.

Alternatively, testing could be done via Internet or using a testing session using the hand held device. This could be done for example during a phone call between the future trainee and the provider using image transfer protocol such as MMS to provide the hand held device with visual stimuli. In some cases, for example when a trainee wants to improve his speed reading abilities, no testing is needed.

After the billing arrangements were made, the training application is loaded 214 to the hand held device.

The method according to the current invention may install an application program in the memory of the hand held device such as a cellular phone. The program may utilize the cellular phone computing power to compute the visual stimuli. Alternately, the stimulation image may be sent from the server 110 on request of the application program using a cellular networking protocol such as SMS or MMS.

Optionally, some of the visual images are generated by the hand held device and other images generated by the server.

In some embodiments of the invention, the application program may run similarly to a cellular phone game.

In one embodiment of the invention, the application program may be loaded to the already existing memory in the cellular phone by a qualified person at distribution location, optionally using appropriate means of interfacing the cellular handset. Alternatively, the application program may be loaded by installing additional memory in existing slot in the handset such as SIMS.

In yet another embodiment, the application program may be loaded by downloading the application wirelessly using the cellular networking protocol.

In this case, the application may be loaded once and used for several sessions or alternatively, the application may be downloaded before each training session.

After the application loading 214 is complete, the trainee may start training session 216.

The steps involve in using other types of hand held device, such as Palm PC, iPod, portable digital game or PDA are similar. Methods of loading program 214 in this case may involve using cable or wireless communication means such as LAN, USB, Infra-Red (IR), Bluetooth, RE-LAN, etc.

Training Session

Figure 2:
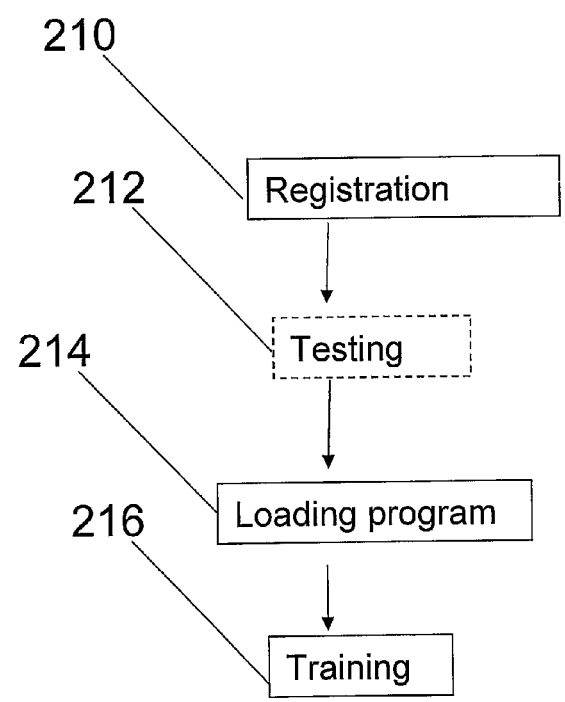
FIG. 2a depicts a method for training the visual system of a human by presenting on a hand held display unit visual stimuli to said human according to an exemplary embodiment of the invention.
FIG. 2b shows some details of training session in a method for training the visual system of a human according to an exemplary embodiment of the invention.
Figure 2:
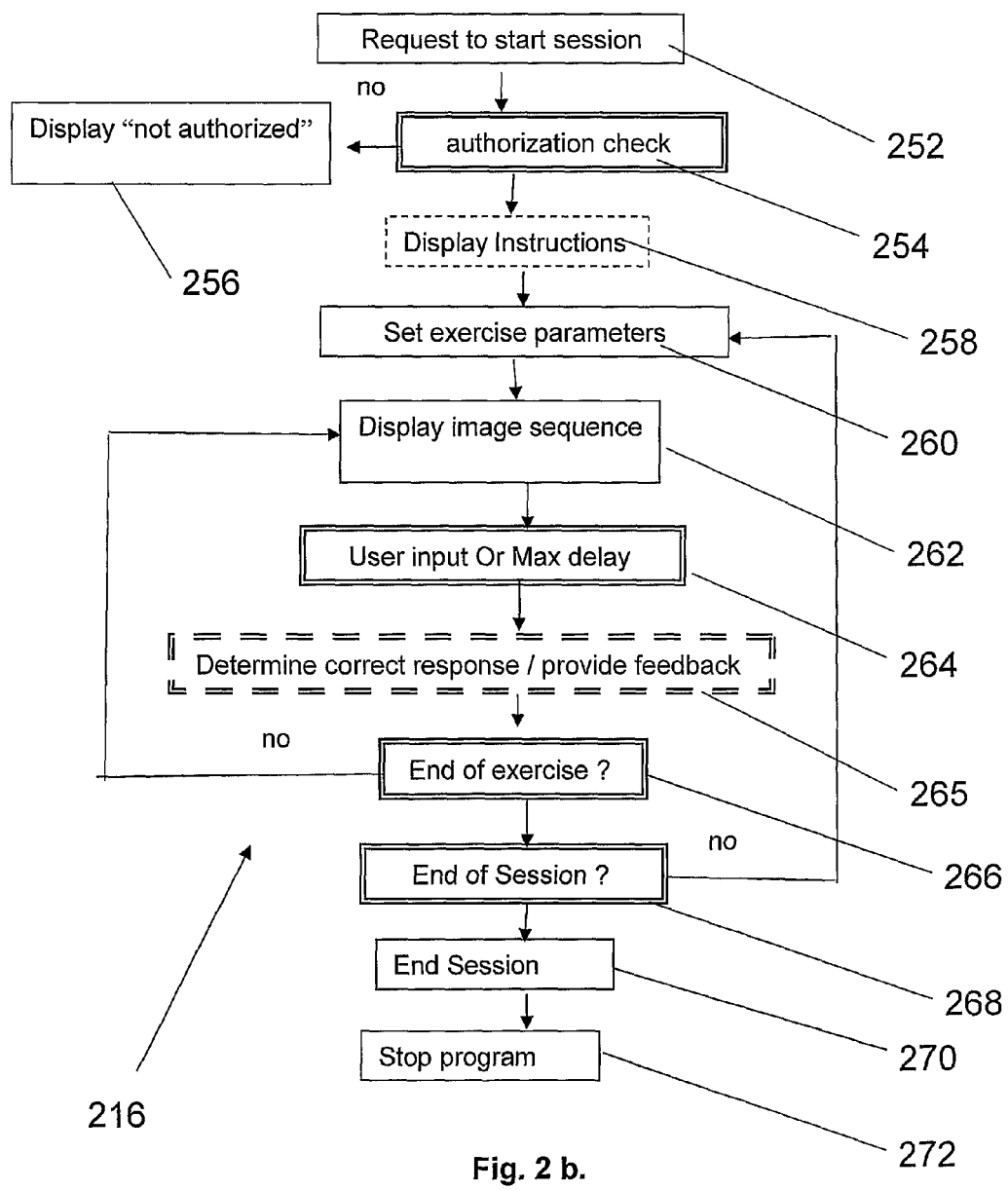

FIG. 2.b. shows some details of training session in a method for training the visual system of a human according to an exemplary embodiment of the invention.

A training session 216 starts when a trainee request a training session 252 by a accessing the application program installed in the hand held device.

The application program performs an authorization check 254 to verify if the user has the right to a training session. This can be done locally within the hand held device or by requesting an authorization from the server 110.

One or combination of few authorization methods may be used: The user may be requested to input a password, the ID of the hand held such as the phone number of a cellular phone may be verified by the server, timely payment or other billing information may be checked by the server, the number of session already exhorted used may be compared to the number of session paid for. Alternatively or additionally, or consistency of past session performance may be analyzed to determine if few different users are sharing the application.

If authorization is not granted, the application may display a warning message such as "session not authorized" message 256, and training session would not start.

If authorization is granted, the application optionally displays instructions 258 for the coming session. An experience trainee may skip the instruction.

Each training session comprises a plurality of exercises. To start an exercise, the application set the exercise parameters 260. Optionally, exercise parameters 260 are preset for all training sessions during loading of the program. Alternatively, computing the exercise parameters may be done on server 110 and be transmitted to the hand held device, or the parameters may be computed by the application in the hand held device.

Optionally, trainee's progress is used to compute the parameters. A qualified person at remote location view from time to time the progress made by the trainee and adjusts the parameters accordingly. In this case, trainee progress is optionally accessed assessed by the qualified person optionally using the Internet.

The parameters define the type of image to be used as visual stimuli, its size, its contrast, sequence of stimuli, the duration of display of each stimulus the delay between images etc. The parameters also define for each visual task what the correct user response 264 is and what is the time interval within which the response should be given 264. Optionally, the parameters also define a maximum time interval after which the task is skipped or the session paused or ends if the user does not respond.

Optionally, the program analyzes the trainee's response and gives it a score based on the type of the response and optionally based on the time of the response.

Optionally a feedback 265 is displayed to the trainee after the visual task. Alternatively, an average score or feedback or both are displayed at the end of an exercise 266 or at the end of a session 270. Generally, parameters for the full Exercise are pre-calculated. The parameters of an image do not necessarily depend on the user response to the preceding task.

Visual Task

In a visual task, the trainee is presented with a visual stimulus or an image sequence 262 and the trainee is requested to observe the image or images and provide a response.

For example, in a visual task the trainee is required to locate a visual target in an image and respond with yes/no if a target was located in an image or not.

Alternatively, a sequence of images can be displayed and the trainee has to identify—when the target appeared or which of the images in the sequence include a target.

Figure 3:
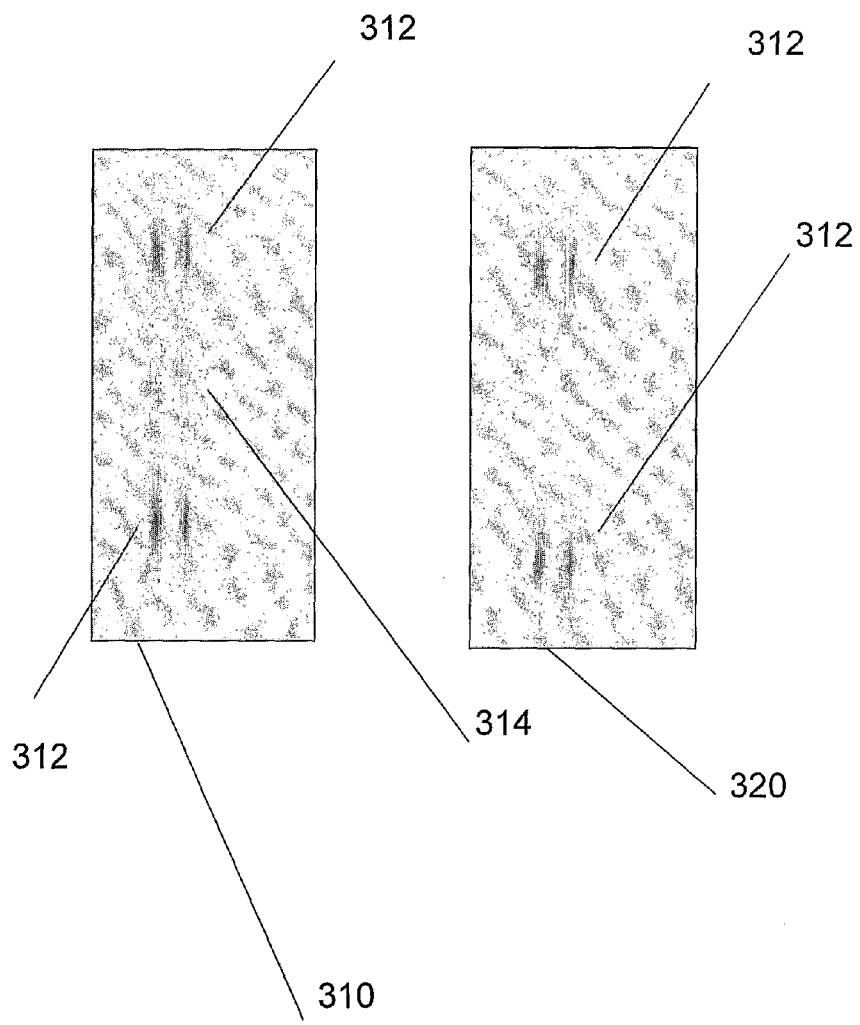
FIG. 3 is an illustration of an embodiment of a visual stimulus for training the visual system of a human as known in the art.

FIG. 3. shows such a sequence. The exemplary sequence consists of two images: first image 310 including target structure 314 and flanking structures 312; and second image 320 including only flanking structures 312. A correct response in this example will be for example pressing the key #1 to identify that the target was in the first image.

Figure 4:
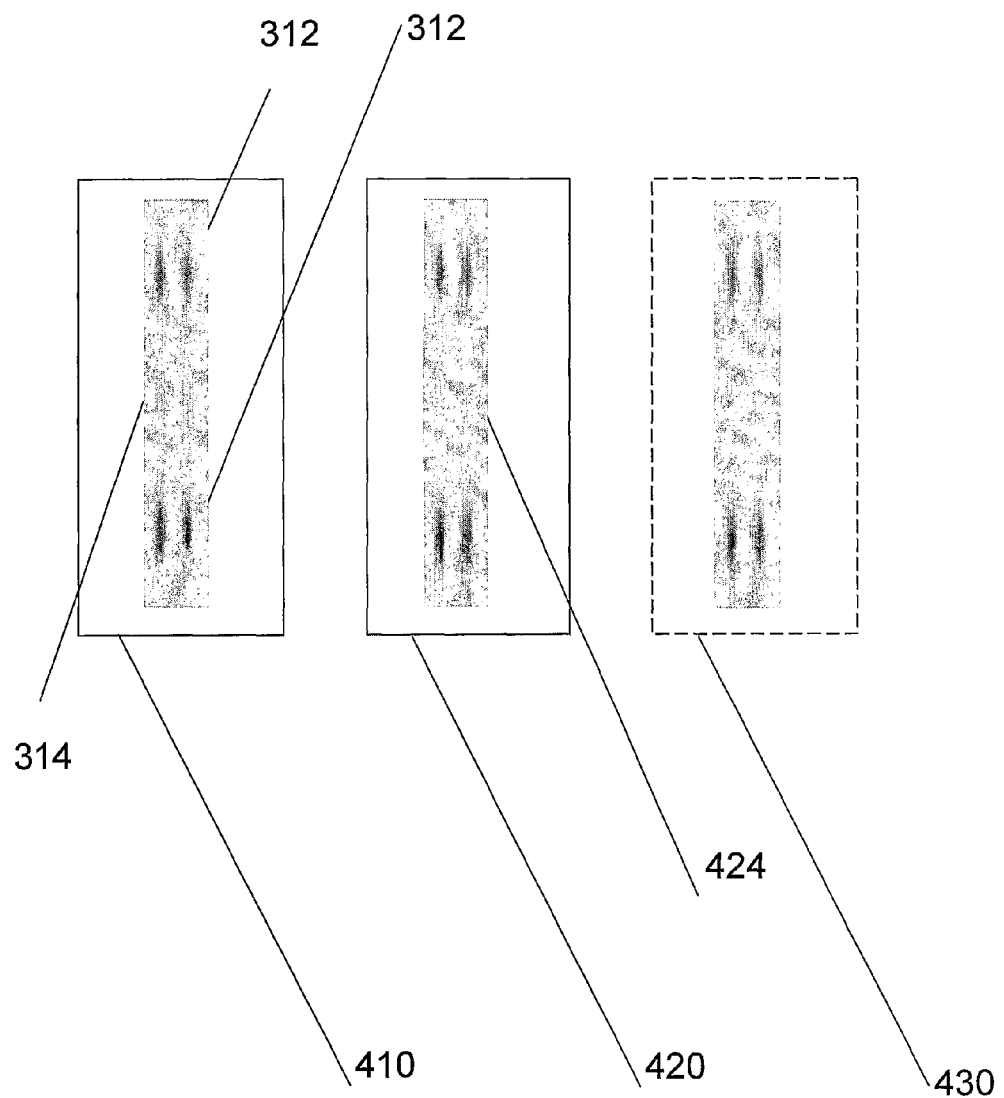
FIG. 4a-to 4c are illustrations of an embodiment of visual stimuli for training the visual system of a human according to some exemplary embodiments of the invention.
Figure 4:
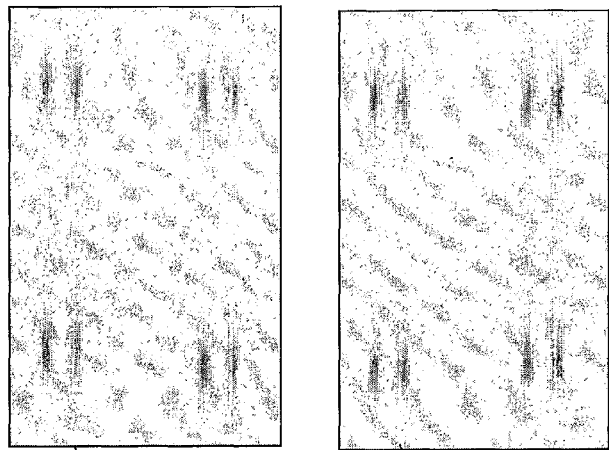
Figure 4:
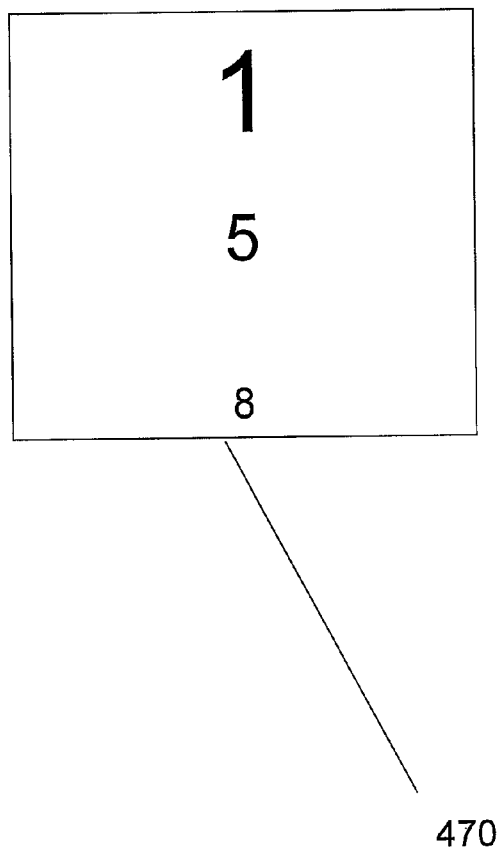

In contrast, FIG. 4.a. shows a sequence of at least two images 410 and 420 each comprises plurality of flanking structure 312 and at least one target structure, but the target structures 314 and 424 are of different strength. Strength of a target may be its size, contrast, difference in shade or color, etc.

Alternatively a sequence of more than two images such as 410, 420 and 430; may be shown, optionally in cyclic manner and the proper user response would be to respond when the target with the highest strength is presented. Alternatively, the visual task may be to identify the absence of a target in one of a sequence of images. Alternatively, flanking structures may be missing and the visual task is to identify a change in the target's strength.

Alternatively, the visual task may be to count the number of images in a sequence. For example, a collection of images, some identical, similar or distinct images may be presented in rapid sequence to the trainee, and his task is to identify the number of images in the sequence, the number or different or identical images in the sequence, etc. Alternatively, or additionally, the visual task may be to identify changes of the presented images.

Similarly, the trainee may be requested to respond by identifying the location of a target within the image such as left/right/up/down. An example for such a task can be seen in FIG. 4.b. where two images are seen: First image 450 in which the target is located on the left and second imager 460 wherein the target location is on the right.

In another embodiment of the invention, at least two images are presented; at least one of these imagers is displayed for a different duration. For example, first image may be displayed for duration of 100 milliseconds and second image for duration of 130 milliseconds. The visual task is to identify the image displayed for longer (or shorter time). It is clear to realize that the task is easy when the times are long and the differences are large.

Training program may start with such easy tasks and progress to more difficult settings.

Numerous combinations of such visual tasks may be created by a person skilled in the art.

In FIG. 4.c. an image 470 in which digits of varying sizes are presented.

Similarly images containing words with of varying length may be presented to the trainee for short duration in order to develop fast reading capabilities. The trainee is than required for example to identify if the image contains a legal word.

Other tasks could be designed for example; an image with slowly increasing target strength wherein the task is to press a key as soon as the location of the target is determined or as soon as the target is observed The task is scored according to the parameters for being the correct response and optionally by the time taken by the trainee to respond.

In another type of visual tasks may be aimed at increasing the speed of visual image processing by the trainee. A sequence of images is shown in with decreasing delay between them.

The sequence of images may comprise a target image following a masking image. The duration of target image display decreases as the trainee improves his score. The target image may be a digit, a number, a letter or a word or an identifiable image.

Figure 5:
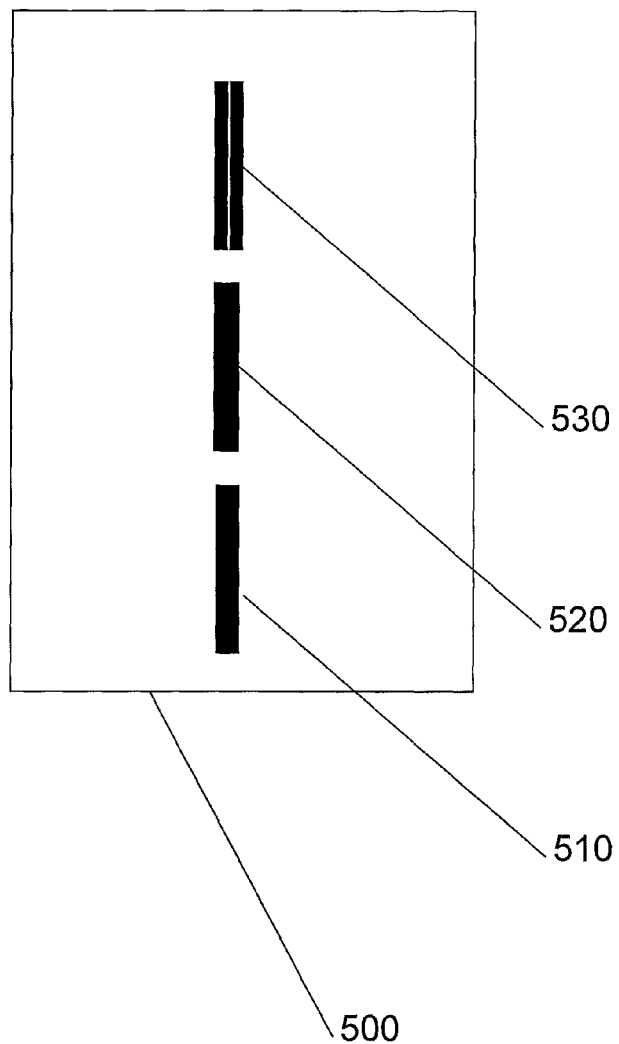
FIG. 5 is an illustration of an embodiment of visual stimuli for training the visual system of a human according to some exemplary embodiments of the invention.

Current researches by the inventor and his colleagues have indicated that training may shorten the speed in which images are processed FIG. 5. is an illustration of an embodiment of visual stimuli for training the visual system of a human, aimed to improving visual resolution. The image 500 includes at least one pair of lines separated by a narrow gap. In the example of FIG. 5, three such pairs are shown: zero gap 510, narrow gap 520 and wide gap 530. The human brain. In the preferred embodiment, a target image is displayed for a short time followed by a masking image which is similar to the target image but with at least one difference. Preferably, the two images are shown at the same or close place in the visual field. The training starts with long time separation between the two images, for example 0.3 to 1 second. As the trainee gain speed, the time interval is shortened. At some short time interval the person no longer able to identify the target due to the masking effect of the second image. In a normal person this time interval is approximately 180 milliseconds. Longer times were observed in dyslectic patients. Experiments have shown that this time may be shortened to 30 milliseconds. Since in everyday life, the human's visual system is "bombarded" with visual signals, the processing speed of the brain is one of the limiting factors to visual perception, and improving it may improve vision without actually changing the optical components of the vision. Similarly, condition of dyslectic patients may improve by this type of training. The lines, gap and background may be in different colors and contrast. The lines may be at various length and orientation.

In this example, trainee is requested to identify the narrow gap.

Figure 6C:
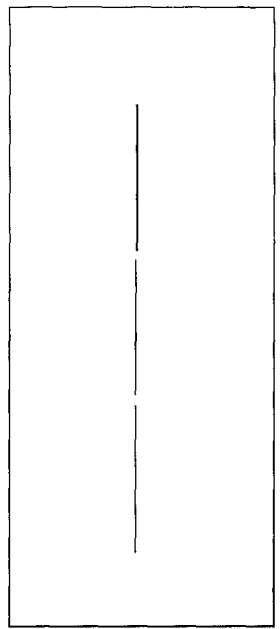
FIGS. 6a to 6c are illustrations of an embodiment of visual stimuli for training the visual system of a human according to some exemplary embodiments of the invention.
Figure 6B:
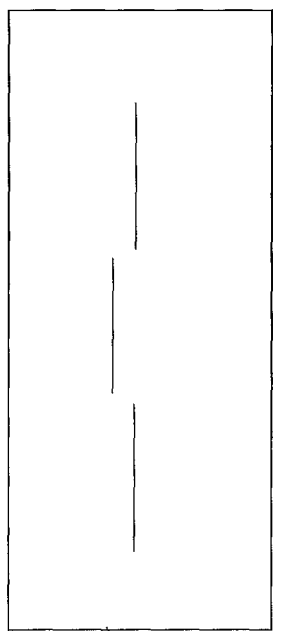
Figure 6A:
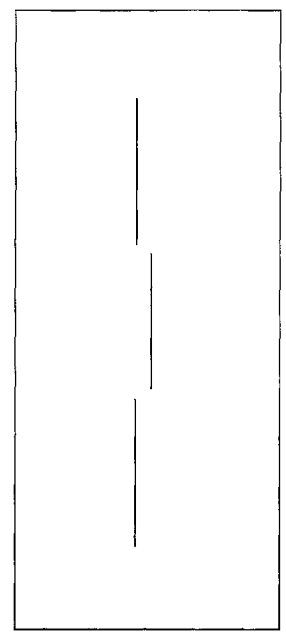

FIG. 6.a. to 6.c. are additional illustrations of an embodiment of visual stimuli. In this example, the trainee is requested to identify in what direction the central section of the line is displaced: to the right as in image 630, to the left as in image 620 or not at all as in image 610.

Figure 7:
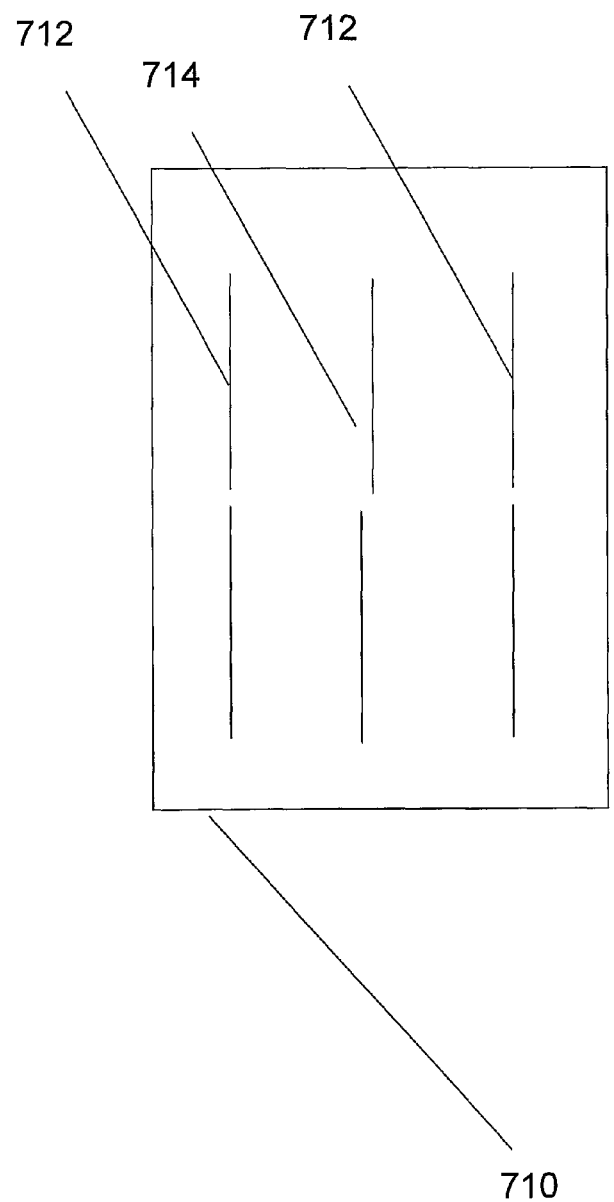
FIG. 7 is an illustration of an embodiment of visual stimuli for training the visual system of a human according to some exemplary embodiments of the invention.

FIG. 7. are additional illustrations of an embodiment of visual stimuli. In this example, the image 710 comprises a target structure 714 and two flanking structures 712. The trainee is requested to identify if the top section of the target structure 714 is displaced and if so—in what direction.

Feedback.

Feedback informing the trainee about the degree of his success may be given immediately after the response 265 or as average score at the end of each exercise 266 or at the end of a session 270 or in a combination of few of these methods.

At the end of each exercise, the application determines if the session has reached its end 268. If so, the application is closing the session 270 by optionally providing the trainee a feedback about its progress during the session and optionally transmitting information to the server 110 regarding the session. The application then stops 272.

Optionally, the server receives information at end of each or some of the s or at the end of each or some of the sessions or exercise. Exercise may be scored according to the individual progress of the trainee as judged by his recorded history of his response, optionally compared to average progress by trainee with similar condition.

If during a session, the training is interrupted, for example when the hand held device is a cellular phone and the cellular phone receives an incoming call, the application may be configured to pause for the duration of the call and resume when the call ends. Alternatively, the application may stop on interruption or pause for a maximum duration than stop. The ringer or vibrate mode of a cellular phone may be configured to be active or inactive to allow or prevent interruption by incoming call during the training session.

Optionally, the application may be configured to re-start a task or restart the exercise or restart the session after interruption. If the application is stopped in mid-session, it may be configured to start where it stopped or to re-start the session.

Optionally, a set of exercises may be prepared, each defined by its parameters. Preferably, the exercises are arranged in increasing level of difficulty. The trainee may optionally start a more difficult exercise only if he reached a minimal score in the preceding exercise.

Billing and Means to Avoid Abuse by Unauthorized User.

Several modes of payment can be applicable for the method according to the current invention:

A fixed price could be charged when the application program is installed. This payment may enable the trainee to use the application for a set calendar duration optionally only for a set number of session per day. Alternatively a total of a set number of session are enabled or until a preset progress was made.

Alternatively, a "per-use" fee can be charged, initiated by server 110 whenever a session is requested. Alternatively, "Air-time" fee charged by the cellular network for communication between server 110 and hand held device 118 could be shared with the application provider.

Methods for preventing unauthorized copy or use of computer programs such as hardware key or a password-generating device may be used to protect the application.

Visual acuity evaluation tests are widely used by ophthalmologists and optometrists in assessing vision and ability of a subject to recognize and discern objects. Visual acuity is a measure of the spatial resolution of the visual processing system and is usually tested in a manner to optimize and standardize the conditions. To accomplish this, a board which presents black symbols of varying sizes on a white background (for maximal contrast), is placed at a sufficient distance from the subject so as to approximate infinity (typically some 6 meters away from the subject). The subject is shown the board and is requested to identify the symbols. Typically different letters are used (e.g. Snellen charts). Similarly, charts with the letter E directed in various directions are also used, where the subject is requested to indicate which way the E is directed. Small children are presented with charts which include drawings or other graphic symbols recognizable by children. The symbol board is typically a printed poster hanged on a wall, or a transparent or semi-transparent board with symbols which is lit from behind.

In these vision acuity tests the viewing parameters of the shown symbols are fixed and the subject is required to be distanced several meters away from the board. Other vision acuity tests involve the use of printed charts, which are viewed by the subject from a distance of a few dozens of centimeters (e.g. 33 to 40 cm) and intended to test the reading ability. All above methods test the visual acuity for static conditions, whereas in everyday life, many conditions require to see fast changing or moving images. These transient conditions are more difficult, and are not addressed by the standard visual acuity tests.

According to some embodiments of the present invention, it is an object of the present invention to provide novel system and method for vision evaluation which facilitate performing vision evaluation tests where the subject and the symbols are substantially closer, so that in fact the subject may hold a display and be presented with one or more symbols.

Furthermore, according to some embodiments of the present invention, it is an object of the present invention to provide automated system and method for vision evaluation, for testing the subject and automatically generating a score or other corresponding result, calculated based on responses of the subject which are recorded by the system.

According to embodiments of the present invention, novel method and system for vision evaluation are disclosed herein.

According to embodiments of the present invention a user is subjected to a vision evaluation test, in which a display device is used to display to a subject a sequence of one or more images containing one or more symbols (hereinafter referred to as a "symbol"), while varying one or more parameters of the displayed symbol.

According to embodiments of the present invention, said one or more parameters of the displayed symbol may be, for example, the physical size of the displayed symbol, duration of presentation of the symbol to the user, contrast of the symbol (with respect to its background, or with respect to parts of the symbol), color of the symbol and its background, the number of concurrently presented symbols and resolution of the displayed symbol.

A method for determining the smallest symbol size the user can identify, also known as the "staircase" method, may be used, incorporated in a method for vision evaluation, according to embodiments of the present invention.

A display device, according to embodiments of the present invention, may be a stationary display device, such as for example, a desktop computer monitor, a TV screen, e.g. cathode ray tube (CRT), plasma, liquid crystal display (LCD), an overhead projector. A display device, according to embodiments of the present invention, may be a mobile display device, such as, for example, notebook, a hand-held device, for example, a cellular communication device, personal digital assistant (PDA), iPod™, and iPad™.

According to embodiments of the present invention, the user is requested to respond to the displayed sequence of symbols, for example, by identifying the displayed symbol or by identifying a parameter associated with the symbol (hereinafter referred to as "identifying the symbol"), such as for example, by indicating the direction it is pointing at, its shape, recognizing the symbol or identifying and indicating any other parameter of the symbol, and inputting an appropriate input. The input provided by the user is used by the device to verify the identification of the symbol or the selected parameter of the symbol and it is determined whether or not the user correctly identified the symbol.

The duration of the presentation of each frame, according to embodiments of the present invention may decrease in the course of the vision evaluation test. Each frame of the sequence is presented to the user for a predetermined time, and as the vision evaluation test proceeds the duration of the predetermined time is decreased.

According to embodiments of the present invention, once the user can not identify the symbol the device may automatically generate a score for the vision evaluation test of the user. According to embodiments of the present invention the device may also determine and output the appropriate diopter for the spectacle lenses which should be used by the user in order to fix or enhance his or her subjective vision for this distance.

Figure 8:
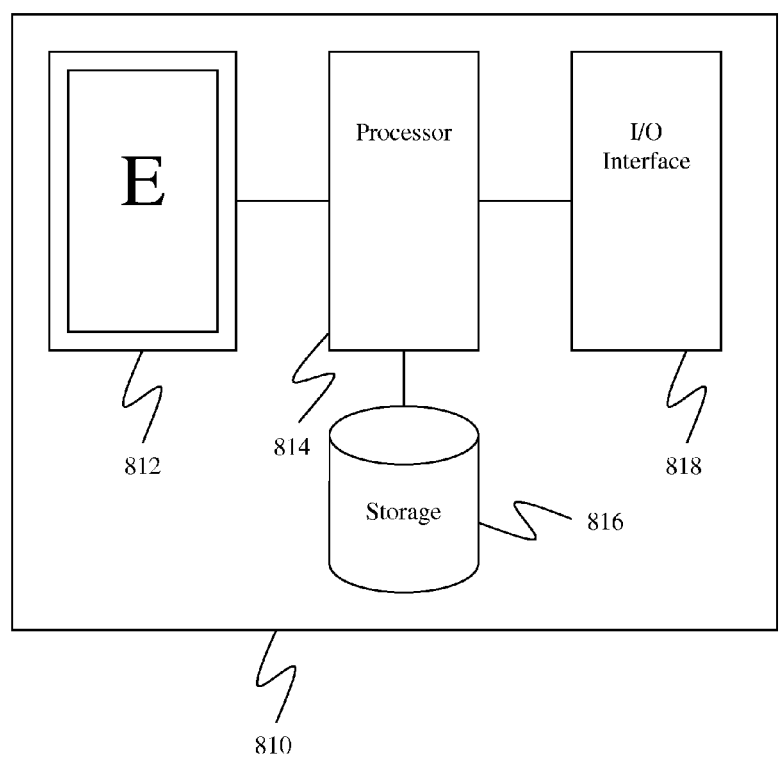
FIG. 8 illustrates a system for vision evaluation, according to embodiments of the present invention.

FIG. 8 illustrates a system 810 for vision evaluation, according to embodiments of the present invention.

System 810 includes display screen 812, processor 814, storage facility 816 and input/output (I/O) interface 818.

Display screen 812 may comprise a desktop computer monitor, a TV screen (CRT, plasma, LCD), a mobile display device, such as, for example, notebook, a hand-held device such as, for example, a cellular communication device, personal digital assistant (PDA), iPod™, iPad™ and the like. Processing unit 814 may be designed to run a computer program stored in storage 816, which performed a vision evaluation test by presenting to a user a sequence of symbols, while changing one or more viewing parameters of the symbols as the sequence progresses. I/O interface 818 is designed to allow the user, upon identifying the symbol currently displayed, to respond to the displayed sequence of symbols by inputting an indication which is verified to determine if the user correctly identified the symbol.

I/O interface 818 may be, for example, a keyboard, a pointing device, an electronic pen or a tracking ball.

I/O interface 818 may also be incorporated with display screen 812 in the form of a touch sensitive screen.

Display screen 812 is used for displaying a sequence of frames, each frame containing one or more symbols, changing one or more viewing parameters between frames of the sequence as the displaying of the frames progresses. Processing unit 14 is used for calculating a vision evaluation score for the subject whose response to the displayed sequence of frames is received through an input interface device.

The score can be, for example in the form of X/Y, where the numerator (X) indicates the distance between the eyes of the subject and the display screen, whereas the denominator (Y) indicates the distance at which the lines that make up the symbols of a frame displayed on the display screen would be separated by a visual angle of 1 arc minute.

Each frame may include a target that includes one or more symbols, for example, letters, numbers, graphical symbols or abstract drawings. When displaying a frame the target may be presented in the center of the screen, and the subject is required identify the displayed target and to respond by inputting a response using the I/O interface device, which distinctly indicates how the subject had identified the target. Each frame may include one or more symbols or two or more symbols. Each frame may include at least one target or at least two targets.

For example, the subject may be shown a series of frames which include, each, the letter E, in one of two positions (facing to the right or to the left, or facing up or down) or one of four positions (facing to the right, to the left, up or down), or, in fact, one of any other number of positions. The subject would then be required to indicate the direction the letter E is facing, by pressing a corresponding key on a keyboard, for example, pressing the appropriate arrow key, or any other key designated to indicate the corresponding direction. Alternatively, the targets may include different letters or symbols and the subject would be required to press on the key corresponding to that letter of symbol.

The display of the sequence of frames progresses until the subject can no longer properly identify the target.

The processing unit then calculates the score based on the most recent response or on all or part of the response information.

Figure 9:
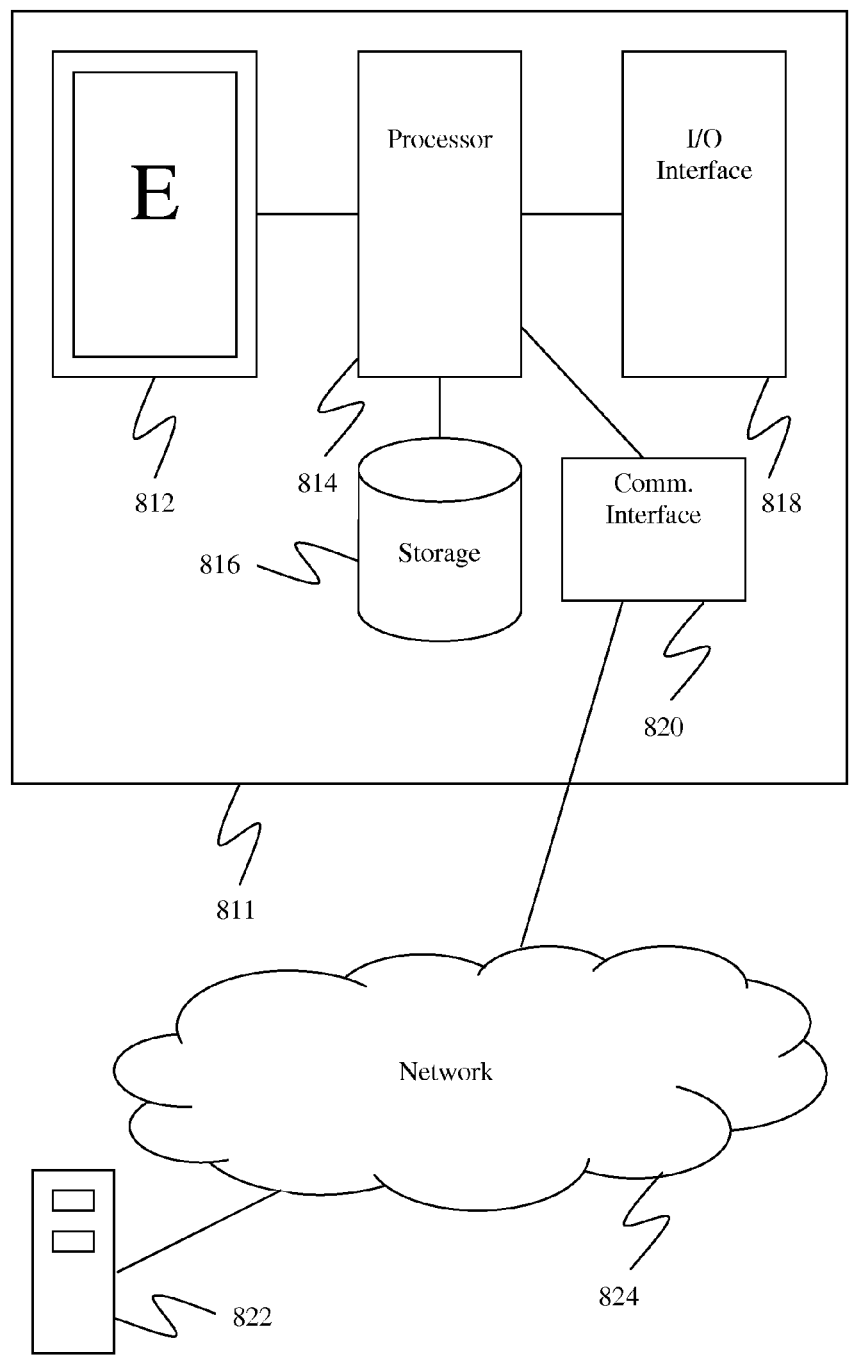
FIG. 9 illustrates a system for vision evaluation, according to other embodiments of the present invention.

FIG. 9 illustrates a system 911 for vision evaluation, according to other embodiments of the present invention.

In the embodiment shown in FIG. 9, system 911 communicates over network 924 with remote server 922. A local application, which may be saved in storage 916 is run on processing unit 914 to display the sequence of frames on the display screen 912, but the responses of the subject, which is input through I/O interface device 918 is communicated via communication interface 920, over network 24 to remote server 922, where the calculation is carried out.

Figure 10:
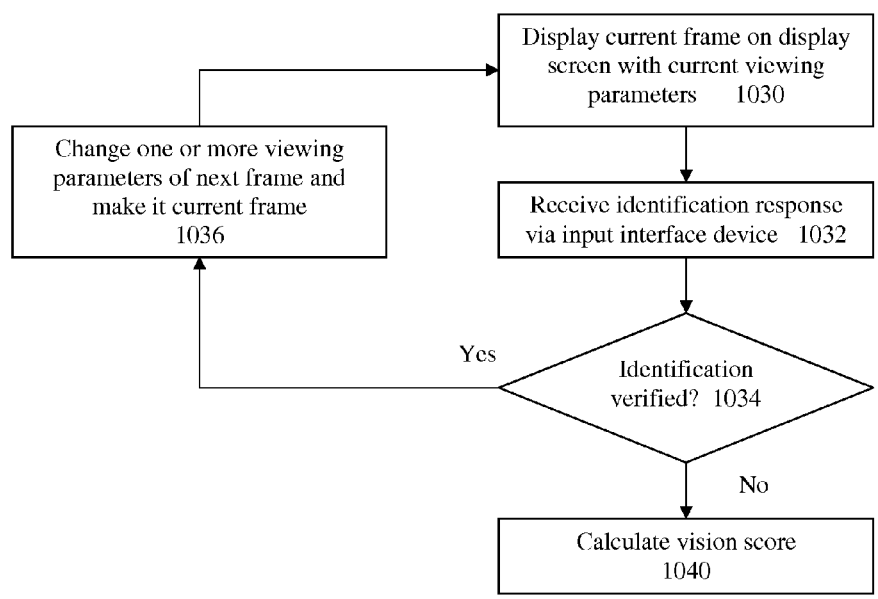
FIG. 10 illustrates a flow chart of a method for vision evaluation, according to embodiments of the present invention.

FIG. 10 illustrates a flow chart of a method for vision evaluation, according to embodiments of the present invention.

A first (current) frame including the target is displayed to the subject in the display screen with initial (current) viewing parameters 1030. The subject then inputs an identification response via the input interface device 1032. The identification response is examined by the processing unit to verify whether the identification is correct 1034. If the identification is correct, one or more viewing parameters of the next frame are changed and it is indicated as the current frame 1036. This next frame (now the current frame) is displayed on the display screen with the (new) current viewing parameters 1030, and the following steps are repeated.

If the identification is incorrect, vision score for the subject is calculated 40.

The viewing parameters which are changed as the display of the sequence of frames progresses may include one or more of the following parameters:

Physical size of the target. Visual acuity is a measure of the spatial resolution of the visual system, which includes the optical part of the eye, and the perceptual part in the brain. Vision of 6/6 refers to a resolution of a letter with the total size of 5 arc minute and with the inner details size of 1 arc minute, viewed form a distance of 6 meters. Visual acuity is defined by the smallest identifiable letter size. A vision evaluation test, according to embodiments of the present invention may cover the whole range of visual acuity, from 6/60 to the smallest target facilitated by the resolution of the display screen.

Duration of target presentation. The target can be presented for varied periods, starting, for example, from a static presentation (i.e., remaining on the screen until the subject responds) down to 10 milliseconds (ms). The steps in the duration of presentation of a target frame may be limited by the refresh rate of the screen. For instance, for a refresh rate of 100 Hz, each frame may be presented down to 10 ms, whereas for a refresh rate of 50 Hz, the minimal possible duration of displaying of each frame would be 20 ms.

Contrast of the target. The contrast of the target can be varied from very low (e.g. 10%) to high (100%), depending on the duration the display of the target. For long display durations, the contrast may be low, incrementally increasing the contrast as the duration of target display becomes shorter. In accordance with some embodiments of the present invention one can measure the contrast threshold of the target for a plurality of durations (e.g. 30, 60, 90 ms)

Color of the target and the background. The color of the background of a frame may be gray (e.g. 127, when the color scale is ranging between 0 and 255). The color of the target may be varied from black to gray, depending on the chosen contrast. Color variation (different colors) may be used as viewing parameter changes.

The number of presented symbols. For example, in a "single" version of the target, a single E pattern is presented in each frame, whereas in a "crowded" version of the target, a matrix of E patterns (e.g. 5 rows of 5 E's in a row) is presented, each pointing in a random direction. The subject is required, for example, to identify the direction of the central E-pattern (the target) and disregard all the rest, which serve as distracting symbols.

Target resolution. The smallest symbol size used may depend on the screen parameters of size and resolution. For example, the pattern of the letter E is composed of 5 horizontal lines: 3 back, interleaved with 2 white, implying that the minimal possible letter can be composed of 5 pixels in the vertical direction (and a 5 pixels width, in order to keep it suitable for measuring the VA). The successive targets of E pattern sizes would be, for example, composed by products of 5 (i.e., 10, 15, 20, and so on). The largest possible target size depends too on size limitations screen.

When performing a visual evaluation test according to embodiments of the present invention "staircase" technique may be used. The "staircase" technique involves an initial large sized target, clearly allowing error-free identification. The size of the target is then increased by a predetermined number of pixels after every incorrect response and decreased by a predetermined number of pixels (typically the same number as in the increased target) after three consecutive correct responses. This way, at the beginning of the staircase, the size of the target may be reduced until the subject makes a mistake in the identification response, at which point the staircase reverses and the size of the target is increased until the subject again identifies the target correctly, triggering another reversal. Values for these reversals may then be used in calculating the final score (i.e., determining the threshold size of the target, which is the smallest size that may be perceived by the subject). A 3:1 (or other ratio, e.g. 2:1, 4:1 etc) staircase technique may be used to determine the smallest letter size the subject can identify correctly. The test is terminated after a predetermined number of reversals of the staircase, and the geometric mean of the last predetermined number (e.g. four) reversal values in log units is used as an estimate of the threshold target size. The procedure may be repeated for each duration of the target presentation, e.g. 240, 120, 60, and 30 ms, in this order.

In accordance with some embodiments of the present invention, a combined staircase technique may be used, in which the smallest target perceived by the subject is detected for each contrast level, thus establishing a measure for the relation size-contrast.

A vision evaluation test in accordance with the present invention may be performed binocularly (on both eyes of the subject) or monocularly (on one eye of the subject.

Aspects of the present invention, as may be appreciated by a person skilled in the art, may be embodied in the form of a system, a method or a computer program product. Similarly, aspects of the present invention may be embodied as hardware, software or a combination of both. Aspects of the present invention may be embodied as a computer program product saved on one or more computer readable medium (or mediums) in the form of computer readable program code embodied thereon.

For example, the computer readable medium may be a computer readable signal medium or a computer readable non-transitory storage medium. A computer readable storage medium may be, for example, an electronic, optical, magnetic, electromagnetic, infrared, or semiconductor system, apparatus, or device, or any combination thereof.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Computer program code in embodiments of the present invention may be written in any suitable programming language. The program code may execute on a single computer or a plurality of computers.

Aspects of the present invention are described hereinabove with reference to flowcharts and/or block diagrams depicting methods, systems and computer program products according to embodiments of the invention.

What is claimed is:

1. A method for vision evaluation comprising:
   displaying a sequence of frames on a display screen of a display device, each frame containing one or more symbols, changing one or more viewing parameters between frames of said sequence of frames as the displaying of the sequence of frames progresses; wherein said one or more viewing parameters are selected from the group of viewing parameters consisting of spatial and temporal parameters, and
   calculating a vision evaluation score for the subject whose response to the displayed sequence of frames is received through an input interface device.

2. A method as claimed in claim 1, wherein said one or more viewing parameters are selected from a group of viewing parameters consisting of: physical size of said one or more symbols, duration of presentation of each frame of said sequence of frames, contrast of each frame of said sequence of frames, color of said one or more symbols, color of a background of one or more frames of said sequence of frames, number of symbols in each frame of said sequence of frames and display resolution of each frame of said sequence of frames.

3. A method as claimed in claim 1, wherein the calculated score comprises diopter value for one or more spectacle lenses for the subject.

4. A method as claimed in claim 1, wherein changing one or more viewing parameters of the sequence of frames as the displaying of the sequence of frames progresses is carried out between consequtive frames.

5. A method as claimed in claim 1, wherein the calculation of the vision evaluation score is carried out on a remote device communicating via a network with the display device.

6. A method as claimed in claim 1, wherein the displaying of the sequence of frames comprising using a staircase technique.

7. A system for vision evaluation comprising:
   a display device for displaying a sequence of frames on a display screen of the display device, each frame containing one or more symbols, changing one or more viewing parameters between frames of said sequence of frames as the displaying of the sequence of frames progresses, wherein said one or more viewing parameters are selected from the group of viewing parameters consisting of spatial and temporal parameters; and
   a processing unit for calculating a vision evaluation score for the subject whose response to the displayed sequence of frames is received through an input interface device.

8. A system as claimed in claim 7, wherein said one or more viewing parameters are selected from a group of viewing parameters consisting of: physical size of said one or more symbols, duration of presentation of each frame of said sequence of frames, contrast of each frame of said sequence of frames, color of said one or more symbols, color of a background of one or more frames of said sequence of frames, number of symbols in each frame of said sequence of frames and display resolution of each frame of said sequence of frames.

9. A system as claimed in claim 7, wherein the calculated score comprises diopter value for one or more spectacle lenses for the subject.

10. A system as claimed in claim 7, wherein one or more viewing parameters of the sequence of frames progresses are changed between consequtive frames.

11. A system as claimed in claim 7, wherein the display screen is a screen of a device selected from a group of devices that consists of a desktop computer monitor, a TV screen, cathode ray tube, plasma, liquid crystal display notebook, a hand-held device, a cellular communication device, a personal digital assistant, iPod and iPad.

12. A system as claimed in claim 7, wherein the input interface device is selected from a group of interface devices consisting of keyboard, pointing device, electronic pen and tracking ball.

13. A system as claimed in claim 7, wherein the display screen and the input interface device are incorporated in a touch sensitive screen.

* * * * *